United States Patent
Wolf et al.

(10) Patent No.: US 11,644,454 B2
(45) Date of Patent: May 9, 2023

(54) VERIFICATION METHODS AND AGRONOMIC ENHANCEMENTS FOR CARBON REMOVAL BASED ON ENHANCED ROCK WEATHERING

(71) Applicant: Eion Corp., Princeton, NJ (US)

(72) Inventors: Adam Wolf, Princeton, NJ (US); Elliot Suk-Hyun Chang, Berkeley, CA (US); Alan Robert Tank, Bethesda, MD (US)

(73) Assignee: Eion Corp., Princeton, NJ (US)

( * ) Notice: Subject to any disclaimer, the term of this patent is extended or adjusted under 35 U.S.C. 154(b) by 0 days.

(21) Appl. No.: 17/846,838

(22) Filed: Jun. 22, 2022

(65) Prior Publication Data

US 2022/0404329 A1 Dec. 22, 2022

Related U.S. Application Data

(60) Provisional application No. 63/322,672, filed on Mar. 23, 2022, provisional application No. 63/289,395, filed on Dec. 14, 2021, provisional application No. 63/213,398, filed on Jun. 22, 2021.

(51) Int. Cl.
| | |
|---|---|
| *G01N 33/24* | (2006.01) |
| *H01J 49/10* | (2006.01) |
| *C09K 17/12* | (2006.01) |
| *C09K 11/77* | (2006.01) |

(52) U.S. Cl.
CPC .............. *G01N 33/24* (2013.01); *C09K 11/77* (2013.01); *C09K 17/12* (2013.01); *H01J 49/105* (2013.01)

(58) Field of Classification Search
CPC ........ G01N 33/24; C09K 17/12; C09K 11/77; H01J 49/105
USPC ............................................ 250/282
See application file for complete search history.

(56) References Cited

U.S. PATENT DOCUMENTS

| | | | |
|---|---|---|---|
| 6,753,957 B1 * | 6/2004 | Graft | G01N 21/718 |
| | | | 356/318 |
| 2018/0082794 A1 * | 3/2018 | Millman | H01G 9/0525 |
| 2019/0086381 A1 * | 3/2019 | Millman | H01G 4/2325 |
| 2021/0144935 A1 | 5/2021 | Rampolla | |
| 2022/0065103 A1 * | 3/2022 | Rowe | G01N 33/2823 |

OTHER PUBLICATIONS

Haque et al. "Alkaline Mineral Soil Amendment: A Climate Change 'Stabilization Wedge'?" Energies. 2019; 12 (12):2299. https://doi.org/10.3390/en12122299, Abstract; p. 8, para 2, 3.

Haque et al. "Risk assessment of Ni, Cr, and Si release from alkaline minerals during enhanced weathering" Open Agriculture, vol. 5, No. 1, 2020, doi: https://doi.org/10.1515/opag-2020-0016, Abstract; p. 167 para 4-p. 168 para 1; p. 169, para 2.

(Continued)

*Primary Examiner* — Kiet T Nguyen
(74) *Attorney, Agent, or Firm* — Ulmer & Berne LLP; Vance V. Van Drake, III; Alexander J. Johnson

(57) ABSTRACT

The present disclosure relates to methods of verifying enhanced rock weathering using immobile trace elements found within a mineral amendment. Further disclosed are mineral amendments that enable enhanced rock weathering.

11 Claims, 3 Drawing Sheets

(56) References Cited

OTHER PUBLICATIONS

Paulo et al. "Evaluating feedstocks for carbon dioxide removal by enhanced rock weathering and CO2 mineralization." Applied Geochemistry. Apr. 6, 2021, 129. 104955. 10.1016/j.apgeochem.2021.104955. entire document.

Strefler et al. (2018). "Potential and costs of carbon dioxide removal by enhanced weathering of rocks." Environmental Research Letters. 13. 10.1088/1748-9326/aaa9c4. entire document.

International Search Report and Written Opinion of the International Searching Authority for International Patent App. No. PCT/US22/34546 dated Nov. 15, 2022. (10 pages).

* cited by examiner

VERIFICATION METHODS AND AGRONOMIC ENHANCEMENTS FOR CARBON REMOVAL BASED ON ENHANCED ROCK WEATHERING

CROSS REFERENCE TO RELATED APPLICATIONS

The present applications claims the priority benefit of U.S. Provisional Patent App. Ser. No. 63/322,672, filed Mar. 23, 2022; U.S. Provisional Patent App. Ser. No. 63/289,395, filed Dec. 14, 2021; and U.S. Provisional Patent App. Ser. No. 63/213,398, filed, Jun. 22, 2021; each of the foregoing of which are incorporated herein by reference in their respective entireties.

BACKGROUND

The last several years have witnessed a maturation of carbon markets from lightly scrutinized voluntary markets largely serving to provide positive marketing collateral to familiar consumer brands to rigorous compliance markets with proof-of-performance requirements often involving government and quasi-governmental regulators. There have also been a number of comprehensive proposals for decarbonization of the entire US economy, combining energy production, transportation, cement production, and agriculture. These proposals have included carbon dioxide removal (CDR) techniques as an essential component of the decarbonization plan, with a supportive ecosystem of science, policy, and project evaluation criteria. Within the diverse scope of decarbonization efforts, including renewable energy, biofuel, nature-based solutions, and more technical CDR techniques like direct air capture (DAC), The Oxford Principles have developed a taxonomy for categorizing diverse decarbonization strategies. This taxonomy distinguishes between avoided emissions (for instance, conversion of fossil fuel power to renewable power) and negative emissions (for instance direct air capture); distinguishes between avoided emissions that require storage (for instance carbon capture from a point source and sequestration into the ground) and those that do not require storage (the conversion to renewable energy); and the duration of the storage if so required (for instance, short lived forest carbon sequestration from delayed harvests versus storage of captured carbon in geological formations).

A number of for-profit and non-profit organizations have emerged that employ the Oxford Principles to evaluate proposals, particularly around the rigorous quantification across categories (Table 1). This, in essence, is the scorecard that projects will have to compete on to find acceptance in the industry. All other things equal, cost ends up being the primary driver, but quality is also a key consideration. Thus, historically buyers have been drawn to nature-based solutions that cost between $5-20/tCO$_2$ e (e.g., Corteva Carbon, Indigo Carbon), versus direct air capture projects that cost >$500/tCO$_2$ e (e.g., ClimeWorks). However, there are challenges to these nature-based solutions: recently these nature-based solutions have been subject to intense scrutiny for "gaming" the rules or otherwise failing to deliver prospective rewards. Among the technological solutions, there are a different set of challenges: rigor has been strong, but the reduction in price proportional to increase in deployment has been slow, and the ultimate price of DAC is not expected to drop below $150/tCO$_2$e (Keith et al 2018, https://doi.org/10.1016/j.joule.2018.05.006). In light of these challenges, we have developed a technology around "enhanced rock weathering" (ERW), in which silicate minerals are weathered in acidic soil solution, thus driving the uptake of additional CO$_2$ into dissolved inorganic carbon (DIC) in the soil solution. Our experimental work, life cycle analysis, and techno-economic modeling have indicated that ERW provides the permanence, additionality, and rigorous quantification of a DAC project, the large volume of a carbon capture and storage (CCS) project, and the unit economics of a nature based solution, thus creating a new tool to meet net-zero goals.

Details of Enhanced Rock Weathering

In "enhanced rock weathering" (ERW), silicate minerals are weathered by CO$_2$ from the ambient air which has been dissolved into water, reacting to produce dissolved inorganic carbon that is ultimately stored in the ocean as depicted in FIGS. 1 and 2.

Background Geochemistry

The role of silicate rock weathering in maintaining the CO$_2$ balance of the atmosphere has been recognized for decades, first outlined by renowned chemist Harold Urey in the 1950s. The basic premise of the Urey reaction is that continental collisions release CO$_2$ to the atmosphere from volcanoes, and bring Mg- and Ca-bearing silicate rocks to the surface. The rainwater (H$_2$O) that falls upon these rocks is mildly acidic, as atmospheric CO$_2$ has dissolved in it and formed carbonic acid (H$_2$CO$_3$). For forsterite, the weathering reaction takes place following the form:

$$Mg_2SiO_4 + 4H_2O + 4CO_2 \rightarrow 2Mg^{2+} + 4HCO_3^- + 4H_4SiO_4$$

In this reaction, one mole of forsterite consumes four moles of CO$_2$, so two negatively charged bicarbonate HCO$_3^-$ are created for every one divalent Mg' weathered. Given the molecular weight of forsterite (140 g/mol) and the molecular weight of CO$_2$ (44 g/mol), weathering one metric ton of forsterite removes 1.25 metric tons of CO$_2$ from the atmosphere. In general, such a formula can be used to define the "mineral potential" of a silicate based on its elemental composition:

$$MP \equiv \frac{tCO_2e}{tOre} = \frac{MW_{CO_2}}{100\%}\left(\frac{Mg\%}{MW_{Mg}} + \frac{Ca\%}{MW_{Ca}}\right) * V \quad \text{(Equation 1)}$$

where V is the valence of the cation (2 for Mg and Ca) and MW is the molecular weight.

The rate of weathering is determined by the surface area of the mineral, the acidity (pH) of the soil solution, the temperature of the solution, the availability of CO$_2$ reagent in solution, and the rate of removal of the reaction products by water. One of the key insights into the potential of "enhanced" rock weathering is that the rate of reaction, and thus CO$_2$ removal, can be greatly accelerated by increasing the surface area by pulverization into a fine powder (e.g., less than 100 um), incorporating into an acidic environment (e.g., pH less than 6) with abundant CO2 present, and with steady water flux to remove reaction products to maintain acidity. While this formula defines the potential amount of CO$_2$ that may be removed by weathering, it does not speak to the rate; ancient rock formations testify that the rate of weathering can be extremely slow.

The relationship between silicates (like Mg$_2$SiO$_4$) and dissolved carbonates (like HCO$_3$)) is not necessarily intuitive, as the carbonate system of water involves a number of coupled reactions. Atmospheric CO$_2$ dissolves into water according to an exchange coefficient:

$$CO_{2(aq)} = H_2CO_3 = K_{CO_2} * P_{CO_2}$$

Technically $pCO_2$ is "fugacity" that represents its activity, but, as used herein, it is more or less equivalent to its partial pressure, and $K_{CO_2}$ is the Henry's law coefficient that determines the aqueous $CO_2$ in equilibrium with the atmosphere. This aqueous $CO_2$ in turn hydrates with $H_2O$ to become carbonic acid ($H_2CO_3$), which dissociates to become bicarbonate ($HCO_3^-$) and carbonate ($CO_3^{2-}$):

$$H_2CO_3 \leftrightarrow HCO_3^- H^+$$

$$HCO_3^- \leftrightarrow CO_3^{2-} H^+$$

These equilibrium reactions are defined by K1 and K2, the first and second carbonate system dissociation constants. pK1 and pK2 are about 5.9 and about 9.4 at STP, so greater than 99% of the charge in the dissolved carbonates is $HCO_3^-$.

The carbonates are the largest constituents of total alkalinity, which is defined as the charge imbalance between weak acids (proton acceptors) minus proton donors:

$$TA = [HCO_3^-] + 2 \cdot [CO_3^{2-}] + [OH^-] - [H^+]$$

There is an alternative definition of total alkalinity as the charge imbalance between conserved cations and conserved anions:

$$TA = [Na^+] + 2[Mg^{2+}] 2[Ca^{2+}] + [K^+] + \ldots - [Cl^-] - 2[SO_4^{2-}] - [NO_3^-]$$

These two expressions are always equal (i.e. the charges balance). This means that an added Mg or Ca into soil solution will increase in $HCO_3$ to balance the charge. We describe an analytical solution to compute how much carbon is taken up per unit of additional Mg or Ca. If we first define DIC as the sum of $H_2CO_3$, $HCO_3^-$, and $CO_3^{2-}$, and make use of the equilibrium equations above (defining $H^+$ as "h" and $H_2CO_3$ as "s"):

$$DIC = s \cdot \left[ 1 + \frac{K_1}{h} + \frac{K_1 K_2}{h^2} \right]$$

And formulate TA using the same convention:

$$TA = s \cdot \frac{K_1}{h} + s \cdot 2 \cdot \frac{K_1 K_2}{h^2} + \frac{K_w}{h} - h$$

With these definitions in place, we can develop an estimate of dDIC/dTA. First, we compute the derivative dTA/dh:

$$\frac{dTA}{dh} = -s \cdot \left( \frac{K_1}{h^2} + 4 \cdot \frac{K_1 K_2}{h^3} \right) - \frac{K_w}{h^2} - 1$$

Next we compute the derivative dDIC/dh:

$$\frac{dDIC}{dh} = -s \cdot \left( \frac{K_1}{h^2} + 2 \cdot \frac{K_1 K_2}{h^3} \right)$$

Finally we multiply dDIC/dh by the inverse of dTA/dh to calculate dDIC/dTA:

$$\frac{dDIC}{dTA} = \frac{dDIC}{dh} \cdot \frac{dh}{dTA}$$

At the pH found in soils, each Mg or Ca is matched by two carbon atoms. In all circumstances, raising alkalinity results in increased pH. This is particularly important in marine settings, where ocean acidification from increased atmospheric $CO_2$ can be ameliorated by this export of alkalinity from land.

The potential for ERW as a commercial enterprise is limited by some fundamental issues:

A. The total amounts of mineral transformation and carbon removal should be verifiable empirically. The verification methods described below may be low cost at scale, can be performed at arm's length by a 3rd party, and may have safeguards to eliminate fraud.

Additionally, the commercial potential for ERW could be enhanced by a number of different features. Embodiments may include:

B. Processes and modifications of the engineered mineral product that enhance the agronomic performance and ecosystem co-benefits of the engineered mineral.

C. Processes and modifications of the engineered mineral product that control or enhance the mineral dissolution rate of the engineered mineral in soil environments and thus the rate of removal of $CO_2$.

DETAILED DESCRIPTION

Figure 1:
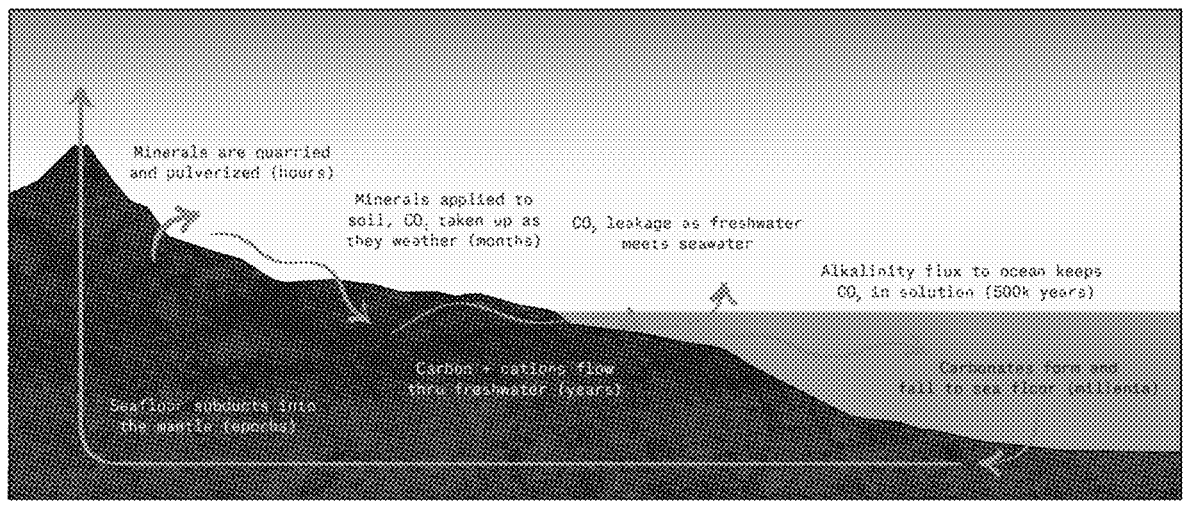
FIG. 1 is a drawing illustrating the enhanced rock weathering cycle.

Summary: The following described methodologies can establish one version of a verification scheme that will demonstrate the transformation of the applied rock material and the subsequent carbon removal into secure geologic reservoirs as evidenced by observations collected from the soil. One set of methods (A) can measure the production of free ions from the applied material and the transport of those ions outside of a control volume as a direct measure of the amount of weathering and thus total carbon dioxide equivalent isolated from the atmosphere. Furthermore, as the elemental inputs into the soil induced by enhanced rock weathering can have significant effects on the soil geochemistry, methods in (B) describe systems and versions that can enhance the agronomic performance of the soil amendment and increase ecosystem co-benefits. Lastly, methods in (C) elaborate on versions that control and enhance the mineral dissolution rate, which increases the financial performance of enhanced rock weathering technology in the marketplace.

A. Systems and Methods for Monitoring and Verification:
Described below are several example methodologies for quantifying the rate and extent of mineral transformation and carbon removal, which are referred to as "verification methodologies".

1. Example Verification methodology 1:
   a. A cation exchange resin and/or an anion exchange resin are packaged into a physical embodiment (such as a 5 cm diameter tube, 5 cm in length, placed 30 cm below the soil surface) that allows vertical transport of fluids but not horizontal transport.

b. Commercial ion exchange resins are pre-equilibrated in such a way that their selectivity is high for the relevant ions, but their capacity is also sufficiently high such that saturation is minimized. This technology may allow for effective deployment for long periods of time, allowing passage of up to 4000 mm of moisture through the tube, without becoming saturated with respect to the ions of interest.

c. The ions of interest are restricted to divalent cations ($Mg^{2+}$, $Ca^{2+}$), carbonate species ($HCO_3^-$ and $CO_3^{2-}$), and silicic acid ($H_4SiO_4$), important weathering products of preferred mineral soil amendments, such as ultramafic rocks, blast furnace slag, and other naturally occurring or industrial silicate minerals with high Mg and Ca content.

d. Three pre-equilibrated tubes are emplaced fully under the soil below a control depth (e.g., 30 cm, a typical depth of cultivation). This may be done by removing the top 30 cm soil with a shovel or auger, then gently placing the tube in the created void space. Following a certain period of time post-surface application of mineral soil amendment (e.g., 9 to 12 months after application), the tubes are retrieved, and the ions captured within the resin exchanges are measured using standard methodologies, such as ICP-OES and ICP-MS based concentration measurements. Three tubes are used to determine standard deviation error in triplicate.

e. By the principle of charge balance and known thermodynamic reactions taking place in the top 30 cm of soils, the amount of carbonate can be inferred purely from the measurement of cations, under certain assumptions and auxiliary geochemical data. By the addition of more specific anion exchange resins, such as styrene-divinylbenzene, these assumptions can be avoided to get a more precise answer. The increase in cation concentration in the subsurface soil pore water allows for the stoichiometric determination of carbon removal from the gas phase (ambient air).

f. The total carbon dioxide removed during the deployment period may be estimated as equal to the molecular mass of $CO_2$ (44 g/mol) multiplied by the sum of the number of moles of carbonate and two times the number of moles of bicarbonate, multiplied by the area on which mineral was applied to the field, divided by the cross-sectional area of the tube.

g. Direct measurement of aqueous bicarbonate and carbonate species, which are the most readily available forms of carbon induced by a gas exchange of carbon dioxide with the soil pore water, may be conducted using the specified anion exchange resin above. The expression as described in clause (f) explains the calculation used to convert this direct measurement of carbon to an absolute value of carbon dioxide removed during a specified application period.

h. Verification methodology 1 has the advantage that it can provide a direct measure of carbon flux and employs a measurement technique that is mature.

i. However, potential disadvantages may include the need for manufacturing (and its attendant demand for working capital); devices may occasionally be defective; emplacement of a device may alter the flow paths of water, which in turn alters the inferred ion fluxes; emplacement of a device may depend on the user; the knowledge of the location of emplacement may invite manipulation by a stakeholder involved in a carbon transaction; and others.

2. Example Verification methodology 2:

a. The principle behind Verification methodology 2 is that minerals applied for purposes of enhanced rock weathering contain, in addition to the elements outlined above that participate in the weathering reaction (i.e., magnesium, calcium, iron, silicon, oxygen, hydrogen), additional elements in trace amounts. These additional trace elements (TEs) might include rare earth elements (REEs), rare metals (RM), other transition metals (TMs), or a combination thereof. Unlike the primary weathering products that are readily dissolved in solution and lost by leaching, some TEs are strongly bound to mineral and biological surfaces and do not readily leach from the soil control volume (e.g., the top 10 to 30 cm of soil), and are not removed by plants at the concentrations present in our applied rock. These strongly bound trace elements are referred to herein as immobile trace elements (ITEs). Thus, a measure of cumulative cation flux and carbon removal can be computed by comparing the ratio of the lost weathering products, such as magnesium, to ITEs, after accounting for background concentrations of ITEs in the initial soil.

b. As used herein, rare earth elements include scandium (Sc), yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), lutetium (Lu) or a combination thereof. As used herein, rare metals include beryllium (Be), cesium (Cs), gallium (Ga), germanium (Ge), hafnium (Hf), niobium (Nb), rubidium (Rb), tantalum (Ta), zirconium (Zr), or a combination thereof. As used herein, transition metals include nickel (Ni), chromium (Cr), and zinc (Zn) among others and may include a combination of transition metals.

c. An approach based on ITEs depends on the degree of immobility of the element in soil environments, the time horizon after which the ITEs will be measured to estimate carbon removal, the abundance of ITEs in both the soil and the mineral added, and the analytical chemistry used to measure this abundance. An analytical technique that has low detectability thresholds for slightly mobile elements could be sufficient for relatively abundant (e.g., parts per thousand to parts per million) elements over short time horizons (e.g., weeks to months). On the other hand, a different analytical technique could be used over longer time horizons, which in turn could involve quantification of very immobile elements that are present in much lower abundance (e.g., parts per billion to parts per trillion). The approach may be chosen based at least in part on cost, which ITEs are actually conserved, over which time horizons, as well as the performance of the analytical performance used.

d. The relative proportions of ITEs in a sample (rock or soil) constitute a type of unique fingerprint of the material. Because the cost of pure ITEs is large, and the analytical chemistry is not widely available, there is a significant barrier to engineering a fraudulent sample to reproduce the native ITE fingerprint of a mineral soil amendment. Thus, it would be challenging for a stakeholder in a carbon exchange transaction to generate a result that produces the anticipated result (a high or low amount of carbon removal) while also matching the ITE fingerprint generated by a bona fide sample. This is a contrast with measurement schemes for soil organic carbon, in which the landowner or other interested party has an information advantage in terms of where or when to sample, which could be used to achieve a particular carbon measurement objective (high or low).

e. Verification Methodology 2 (VM2) has advantages over Verification Methodology 1 (VM1) in that it avoids the need for the use of a device, which avoids altering the soil hydrology or physical environment in a way that would impact the observed elemental analysis.

f. VM2 may have an advantage over VM1 in not requiring tracking of a specific location for recovering the sampling column.

g. VM2 does, however, include measurement techniques that are less widely available; requires specialized instruments and personnel; requires additional boundary conditions to compute carbon flux (e.g., pre-application soil and rock elemental analysis); and employs assumptions as to the relationship between cation flux and carbon flux.

h. Like VM1, VM2 uses the total amount of mineral applied and the field area, which could be measured, for example, using a digital as-applied map commonly accompanying crops input machinery, or truck weights before and after mineral delivery. This will be referred to as the nominal application rate ($AR_{nominal}$).

i. There are four main calculations in VM2. To the extent any one of these factors is known unambiguously from other sources, each step in VM2 could be used in isolation from the others.
  i. Classify, using ITE fingerprinting, whether a soil has had a specific mineral applied, which may be asserted by an entity wishing to make a claim;
  ii. Calculate, using ITE fingerprinting, what the actual mineral application rate ($AR_{actual}$) for a specific soil sample was, which will necessarily differ in a systematic or random way from the average rate for the entire field;
  iii. Calculate the amount of divalent cations remaining in a control volume relative to the amount predicted by the application rate in (ii) above;
  iv. Calculate, using the fraction computed in (iii) and the mineral potential (Equation 1) computed for the feedstock identified in (i) above, the amount of carbon dioxide removed.

j. In one non-limiting embodiment, the verification methodology to classify whether the claimed mineral applied is the actual mineral applied is as follows:
  i. Collect a sample from mineral to be applied, place in a secure vessel and seal with another secondary bag in order to reach air-tight containment. Label as Mineral Amendment.
  ii. Prior to mineral application, collect a 20 g sample from cultivated zone of soil (typically at around 30 cm, such as in a range of 0 cm to 30 cm), place in a secure vessel and seal with another secondary bag in order to reach air-tight containment. Label as Soil A.
  iii. Subsequent to mineral application, collect a 20 g sample the same control zone as soil A, and store under similar conditions. Label as Soil B. Soil B could be sampled immediately after mineral application or at a later time (e.g., months to years afterwards).
  iv. Characterize the elemental composition of Mineral Amendment, Soil A, and Soil B. Example approaches to characterizing the elemental composition are described in (v) and (vi).
  v. One approach to measuring the elemental composition is as follows:
    1. In a laboratory setting, unseal the soil samples and place 10 grams of Soil A and Soil B in two separate beakers.
    2. Dissolve the solids in strong acid. For example, add 21 mL of strong 1.0 M hydrochloric acid and 7 mL of strong 1.0 M nitric acid (total 28 mL acid) to each beaker of sterilized soil and stir rigorously until solids are dissolved.
    3. Filter the sample-containing beakers first through a 1- to 5-micron water filter cartridge followed by an attached 10 to 20 cm column cation exchange resin at a sufficiently slow flow rate of, for example, 1 to 5 mL/min. This combination of a water filter with a cation exchange column has been engineered for optimal performance with soils under consideration. Specifically, the 5-micron water filter cartridge separates out any larger particles, allowing for the smaller particles to exchange its bound metals with the subsequent cation exchange resin.
    4. Flush copious amounts (e.g., 100-200 mL) of 0.5 to 1.0 M chelator such as, for example, ethylenediaminetetraacetic acid (EDTA) at 1-5 mL/min through the used filters into their respective filtrates. This may collect any additional metals that were still adhered to the filters.
    5. Send filtrate A (resultant sample from Soil A) and filtrate B (resultant sample from Soil B) to an analytical laboratory for analysis on an inductively coupled plasma mass spectrometer (ICP-MS). Measurements may include concentrations of high ppb detection of REEs, high ppm detection of Mg, and percent mineralogical fractions of $SiO_2$, $Al_2O_3$, and $Fe_2O_3$.
    6. The ICP-MS may be set to detect magnesium concentrations and the following 17 elements on a high ppb or low ppm detection level: Yttrium, Scandium, Lanthanum, Cerium, Praseodymium, Neodymium, Promethium, Samarium, Europium, Gadolinium, Terbium, Dysprosium, Holmium, Erbium, Thulium, Ytterbium, Lutetium. Classify light rare earth elements (LREEs) as yttrium, scandium, lanthanum, cerium, praseodymium, neodymium, promethium, and samarium. Classify heavy rare earth elements (HREEs) as europium, gadolinium, terbium, dysprosium, holmium, erbium, thulium, ytterbium, and lutetium. Send an isolated rock material sample for ICP-MS analysis. Similar to the filtrate analyses, measurements may include concentrations of high ppb detection of REEs, high ppm detection of Mg, and percent mineralogical fractions of SiO2, Al2O3, and Fe2O3.

vi. Another approach to measuring the elemental composition is as follows:
1. Calibrate a portable XRF instrument for particularly low detection limit of ITEs using a calibration standard (such as Bruker proprietary Geo calibration+custom ITE standards).
2. Use the portable XRF instrument to analyze the Rock Material and Soil A for ITEs (as identified in Verification methodology 2), reporting the instrumental error (2 standard deviations) as well.
3. Use the portable XRF instrument to analyze Soil B for ITEs, reporting the instrumental error (2 standard deviations) as well.

vii. Once the above elemental composition has been determined, calculate the difference for every element between Mineral Amendment and Soil A, resulting in a vector of differences $v_{rock}$. Likewise, compute the difference for every element between Soil B and Soil A, resulting in a vector of differences $v_{soil}$. To improve performance, each element may be divided by an individual factor, such as the detection threshold, or the instrumental uncertainty, or the elemental composition of a reference material. Another means to improve performance would be to sum a subset of the elements or several distinct subsets of elements before computing $v_{rock}$ and $v_{soil}$. Another means to improve performance would be to compute indices of these summed subsets of elements, for example the ratio of the light REEs to the heavy REEs, before computing $v_{rock}$ and $v_{soil}$.

viii. Compute the dot product of $v_{rock}$ and $v_{soil}$. If the value of this dot product is close to 1 (e.g., within a threshold value), then the Soil B is positively classified as having the Mineral Amendment. If the value of the dot product is less than 1 minus a threshold value, then Soil B is negatively classified as not having the Mineral Amendment.

ix. The threshold value may be determined using a variety of means, for example the half-angle between the dot product of $v_{rock}$ and $v_{soil}$ and any other known $v_{rock}$ and $v_{soil}$; or using a Monte Carlo simulation of $v_{rock}$ and $v_{soil}$ that accounts for known sources of uncertainty including instrumental error, variation in rock elemental analysis, or variation of soil elemental analysis.

k. In one non-limiting embodiment, the verification methodology to calculate the actual mineral application rate ($AR_{actual}$) for a specific soil sample is as follows:
i. Characterize the elemental composition the elemental composition of Mineral Amendment, Soil A, and Soil B as above. Note that there could be different analytical chemistry employed if, for example, rapid and inexpensive XRF analysis was used for classification soon after application, and slower and more costly ICP analysis may be used to estimate application rates.
ii. Compute the differences in elemental composition as above, potentially including similar performance enhancements such as normalizing by factors specific to each element, summing across subsets of elements, and computing indices such as the ratio of light REEs to heavy REEs. Such transformed and summed variables for a sample will be referred to generically as $\Sigma ITE_{sample}$.
iii. The actual application rate of the sample can be calculated using the following expression:

$$ARactual = x\left[\frac{(\sum ITEs_{soilB} - \sum ITEs_{soilA})}{(\sum ITEs_{mineral})}\right] \quad \text{(Equation 2)}$$

l. In one non-limiting embodiment, the verification methodology to calculate the amount of divalent cations remaining in a control volume relative to the amount predicted by the actual mineral application rate ($AR_{actual}$) as follows:
i. The amount of divalent cations applied (DCapplied) can be calculated by the proven identity of the mineral additive and the actual application rate:

$$DCapplied = AR_{actual} * [Mg_{mineral} Ca_{mineral}] \quad \text{(Equation 3)}$$

where divalent cations are generally restricted in this context to Mg and Ca, and $Mg_{mineral}$ and $Ca_{mineral}$ is the fractional composition of the mineral additive.

ii. The amount of divalent cations remaining (DCremain) in the soil could be estimated using the same elemental analysis as previously (if, for example, ICP-MS was used), or determined from the same sample using a different analysis (if, for example XRF was used and Mg was not measured).

iii. The fractional progress of carbon dioxide removal (CDR) can be estimated by the ratio of remaining divalent cations to applied divalent cations:

$$f_{CDR} = \frac{DCremain}{DCapplied} \quad \text{(Equation 4)}$$

m. In one non-limiting embodiment, the verification methodology to calculate the amount of carbon dioxide removed from the control volume is as follows:
i. Assembling MP, $f_{CDR}$, $AR_{nominal}$ and the land area applied, the total carbon dioxide removal is:

$$CDR = f_{CDR} * MP * AR_{nominal} * Area \quad \text{(Equation 5)}$$

n. While Verification Methodology 2 presented herein provides a broad framework for the detection and application of soil-bound ITEs to estimate long-term geologic carbon drawdown, the efficacy of the approach can also be improved through the focus on specific subsets of ITEs. Non-limiting embodiments of such improvements are listed below:
i. The ITEs specified in equation 2, e.g., ($\Sigma ITEs_{soil\ B}$), may in fact be represented not by the full summation of 17 REEs but instead by the use of only LREEs or the use of only HREEs, as defined in clause xii. Such a calculation would mean the sum of only LREEs in the calculation (yttrium, scandium, lanthanum, cerium, praseodymium, neodymium, promethium, and samarium) or the sum of only HREEs in the calculation (europium, gadolinium, terbium, dysprosium, holmium, erbium, thulium, ytterbium, and lutetium).

ii. Within the use of only LREEs for the calculation (yttrium, scandium, lanthanum, cerium, praseodymium, neodymium, promethium, and samarium), some LREEs may serve as immobile elements more effectively than others. In order to establish an acceptable average and standard deviation for the C drawdown calculation, a subset of the individual LREEs are selected. For example, the subset may include three LREEs. The calculation (equation 2) is conducted for each of the 3 LREEs individually, and an average and standard deviation is then reported for the CDR calculation. Among the 3 LREEs, the following triplicates are listed as potential, non-limiting candidates of interest: [yttrium, scandium, lanthanum], [cerium, lanthanum, neodymium], [cerium, neodymium, samarium], [yttrium, cerium, neodymium], [scandium, neodymium, samarium].

iii. Within the use of only HREEs for the calculation (europium, gadolinium, terbium, dysprosium, holmium, erbium, thulium, ytterbium, and lutetium), some HREEs may serve as immobile elements more effectively than others. In order to establish an acceptable average and standard deviation for the C drawdown calculation, a subset of the individual HREEs are selected. For example, the subset may include three HREEs. The calculation (equation 2a) is conducted for each of the 3 HREEs individually, and an average and standard deviation is then reported for the CDR calculation. Among the 3 HREEs, the following triplicates are listed as potential, non-limiting candidates of interest: [europium, gadolinium, terbium], [europium, terbium, dysprosium], [dysprosium, erbium, ytterbium], [europium, erbium, ytterbium], [europium, dysprosium, erbium].

iv. In order to establish an acceptable average and standard deviation for the C drawdown calculation, a subset of the individual REEs are selected. For example, the subset may include three REEs Chart 1 represents a non-limiting list of REE triplicates that may enhance the efficacy of this C drawdown calculation.

Chart 1. A Non-Limiting List of 455 REE Triplicates that can be Used to Effectively Triangulate a C Drawdown Estimation ('Y', 'La', 'Ce'), ('Y', 'La', 'Pr'), ('Y', 'La', 'Nd'), ('Y', 'La', 'Sm'), ('Y', 'La', 'Eu'), ('Y', 'La', 'Gd'), ('Y', 'La', 'Tb'), ('Y', 'La', 'Dy'), ('Y', 'La', 'Ho'), ('Y', 'La', 'Er'), ('Y', 'La', 'Tm'), ('Y', 'La', 'Yb'), ('Y', 'La', 'Lu'), ('Y', 'Ce', 'Pr'), ('Y', 'Ce', 'Nd'), ('Y', 'Ce', 'Sm'), ('Y', 'Ce', 'Eu'), ('Y', 'Ce', 'Gd'), ('Y', 'Ce', 'Tb'), ('Y', 'Ce', 'Dy'), ('Y', 'Ce', 'Ho'), ('Y', 'Ce', 'Er'), ('Y', 'Ce', 'Tm'), ('Y', 'Ce', 'Yb'), ('Y', 'Ce', 'Lu'), ('Y', 'Pr', 'Nd'), ('Y', 'Pr', 'Sm'), ('Y', 'Pr', 'Eu'), ('Y', 'Pr', 'Gd'), ('Y', 'Pr', 'Tb'), ('Y', 'Pr', 'Dy'), ('Y', 'Pr', 'Ho'), ('Y', 'Pr', Er'), ('Y', 'Pr', 'Tm'), ('Y', 'Pr', 'Yb'), ('Y', 'Pr', 'Lu'), ('Y', 'Nd', 'Sm'), ('Y', 'Nd', 'Eu'), ('Y', 'Nd', 'Gd'), ('Y', 'Nd', 'Tb'), ('Y', 'Nd', 'Dy'), ('Y', 'Nd', 'Ho'), ('Y', 'Nd', 'Er'), ('Y', 'Nd', 'Tm'), ('Y', 'Nd', 'Yb'), ('Y', 'Nd', 'Lu'), ('Y', 'Sm', 'Eu'), ('Y', 'Sm', 'Gd'), ('Y', 'Sm', 'Tb'), ('Y', 'Sm', 'Dy'), ('Y', 'Sm', 'Ho'), ('Y', 'Sm', 'Er'), ('Y', 'Sm', 'Tm'), ('Y', 'Sm', 'Yb'), ('Y', 'Sm', 'Lu'), ('Y', 'Eu', 'Gd'), ('Y', 'Eu', 'Tb'), ('Y', 'Eu', 'Dy'), ('Y', 'Eu', 'Ho'), ('Y', 'Eu', 'Er'), ('Y', 'Eu', 'Tm'), ('Y', 'Eu', 'Yb'), ('Y', 'Eu', 'Lu'), ('Y', 'Gd', 'Tb'), ('Y', 'Gd', 'Dy'), ('Y', 'Gd', 'Ho'), ('Y', 'Gd', 'Er'), ('Y', 'Gd', 'Tm'), ('Y', ' Gd', 'Yb'), ('Y', 'Gd', 'Lu'), ('Y', 'Tb', 'Dy'), ('Y', 'Tb', 'Ho'), ('Y', 'Tb', 'Er'), ('Y', 'Tb', 'Tm'), ('Y', 'Tb', 'Yb'), ('Y', 'Tb', 'Lu'), ('Y', 'Dy', 'Ho'), ('Y', 'Dy', 'Er'), ('Y', 'Dy', 'Tm'), ('Y', 'Dy', 'Yb'), ('Y', 'Dy', 'Lu'), ('Y', 'Ho', 'Er'), ('Y', 'Ho', 'Tm'), ('Y', 'Ho', 'Yb'), ('Y', 'Ho', 'Lu'), ('Y', 'Er', 'Tm'), ('Y', 'Er', 'Y b'), ('Y', 'Er', 'Lu'), ('Y', 'Tm', 'Yb'), ('Y', 'Tm', 'Lu'), ('Y', 'Yb', 'Lu'), ('La', 'Ce', 'Pr'), ('La', 'Ce', 'Nd'), ('La', 'Ce', 'Sm'), ('La', 'Ce', 'Eu'), ('La', 'Ce', 'Gd'), ('La', 'Ce', 'Tb'), ('La', 'Ce', 'Dy'), ('La', 'Ce', ' Ho'), ('La', 'Ce', 'Er'), ('La', 'Ce', 'Tm'), ('La', 'Ce', 'Yb'), ('La', 'Ce', 'Lu'), ('La', 'Pr', 'Nd'), ('La', 'Pr', 'Sm'), ('La', 'Pr', 'Eu'), ('La', 'Pr', 'Gd'), ('La', 'Pr', 'Tb'), ('La', 'Pr', 'Dy'), ('La', 'Pr', 'Ho'), ('La', 'Pr', ' Er'), ('La', 'Pr', 'Tm'), ('La', 'Pr', 'Yb'), ('La', 'Pr', 'Lu'), ('La', 'Nd', 'Sm'), ('La', 'Nd', 'Eu'), ('La', 'Nd', 'Gd'), ('La', 'Nd', 'Tb'), ('La', 'Nd', 'Dy'), ('La', 'Nd', 'Ho'), ('La', 'Nd', 'Er'), ('La', 'Nd', 'Tm'), ('La', ' Nd', 'Yb'), ('La', 'Nd', 'Lu'), ('La', 'Sm', 'Eu'), ('La', 'Sm', 'Gd'), ('La', 'Sm', 'Tb'), ('La', 'Sm', 'Dy'), ('' La', 'Sm', 'Ho'), ('La', 'Sm', 'Er'), ('La', 'Sm', 'Tm'), ('La', 'Sm', 'Yb'), ('La', 'Sm', 'Lu'), ('La', 'Eu', 'G d'), ('La', 'Eu', 'Tb'), ('La', 'Eu', 'Dy'), ('La', 'Eu', 'Ho'), ('La', 'Eu', 'Er'), ('La', 'Eu', 'Tm'), ('La', 'Eu', ' Yb'), ('La', 'Eu', 'Lu'), ('La', 'Gd', 'Tb'), ('La', 'Gd', 'Dy'), ('La', 'Gd', 'Ho'), ('La', 'Gd', 'Er'), ('La', 'G d', 'Tm'), ('La', 'Gd', 'Yb'), ('La', 'Gd', 'Lu'), ('La', 'Tb', 'Dy'), ('La', 'Tb', 'Ho'), ('La', 'Tb', 'Er'), ('La', 'Tb', 'Tm'), ('La', 'Tb', 'Yb'), ('La', 'Tb', 'Lu'), ('La', 'Dy', 'Ho'), ('La', 'Dy', 'Er'), ('La', 'Dy', 'Tm'), ('L a', 'Dy', 'Yb'), ('La', 'Dy', 'Lu'), ('La', 'Ho', 'Er'), ('La', 'Ho', 'Tm'), ('La', 'Ho', 'Yb'), ('La', 'Ho', 'Lu'), ('La', 'Er', 'Tm'), ('La', 'Er', 'Yb'), ('La', 'Er', 'Lu'), ('La', 'Tm', 'Yb'), ('La', 'Tm', 'Lu'), ('La', 'Yb', 'Lu'), ('Ce', 'Pr', 'Nd'), ('Ce', 'Pr', 'Sm'), ('Ce', 'Pr', 'Eu'), ('Ce', 'Pr', 'Gd'), ('Ce', 'Pr', 'Tb'), ('Ce', 'Pr', 'Dy'), ('Ce', 'Pr', 'Ho'), ('Ce', 'Pr', 'Er'), ('Ce', 'Pr', 'Tm'), ('Ce', 'Pr', 'Yb'), ('Ce', 'Pr', 'Lu'), ('Ce', 'Nd', 'Sm'), ('Ce', 'Nd', 'Eu'), ('Ce', 'Nd', 'Gd'), ('Ce', 'Nd', 'Tb'), ('Ce', 'Nd', 'Dy'), ('Ce', 'Nd', 'Ho'), ('Ce', 'Nd', 'Er'), ('Ce', 'Nd', 'Tm'), ('Ce', 'Nd', 'Yb'), ('Ce', 'Nd', 'Lu'), ('Ce', 'Sm', 'Eu'), ('Ce', 'Sm', 'Gd'), ('Ce', ' Sm', 'Tb'), ('Ce', 'Sm', 'Dy'), ('Ce', 'Sm', 'Ho'), ('Ce', 'Sm', 'Er'), ('Ce', 'Sm', 'Tm'), ('Ce', 'Sm', 'Yb'), ('Ce', 'Sm', 'Lu'), ('Ce', 'Eu', 'Gd'), ('Ce', 'Eu', 'Tb'), ('Ce', 'Eu', 'Dy'), ('Ce', 'Eu', 'Ho'), ('Ce', 'Eu', 'Er'), ('Ce', 'Eu', 'Tm'), ('Ce', 'Eu', 'Yb'), ('Ce', 'Eu', 'Lu'), ('Ce', 'Gd', 'Tb'), ('Ce', 'Gd', 'Dy'), ('Ce', 'Gd', 'Ho'), ('Ce', 'Gd', 'Er'), ('Ce', 'Gd', 'Tm'), ('Ce', 'Gd', 'Yb'), ('Ce', 'Gd', 'Lu'), ('Ce', 'Tb', 'Dy'), ('Ce', ' Tb', 'Ho'), ('Ce', 'Tb', 'Er'), ('Ce', 'Tb', 'Tm'), ('Ce', 'Tb', 'Yb'), ('Ce', 'Tb', 'Lu'), ('Ce', 'Dy', 'Ho'), ('C e', 'Dy', 'Er'), ('Ce', 'Dy', 'Tm'), ('Ce', 'Dy', 'Yb'), ('Ce', 'Dy', 'Lu'), ('Ce', 'Ho', 'Er'), ('Ce', 'Ho', 'Tm'), ('Ce', 'Ho', 'Yb'), ('Ce', 'Ho', 'Lu'), ('Ce', 'Er', 'Tm'), ('Ce', 'Er', 'Yb'), ('Ce', 'Er', 'Lu'), ('Ce', 'Tm', ' Yb'), ('Ce', 'Tm', 'Lu'), ('Ce', 'Yb', 'Lu'), ('Pr', 'Nd', 'Sm'), ('Pr', 'Nd', 'Eu'), ('Pr', 'Nd', 'Gd'), ('Pr', 'N d', 'Tb'), ('Pr', 'Nd', 'Dy'), ('Pr', 'Nd', 'Ho'), ('Pr', 'Nd', 'Er'), ('Pr', 'Nd', 'Tm'), ('Pr', 'Nd', 'Yb'), ('Pr', ' Nd', 'Lu'), ('Pr', 'Sm', 'Eu'), ('Pr', 'Sm', 'Gd'), ('Pr', 'Sm', 'Tb'), ('Pr', 'Sm', 'Dy'), ('Pr', 'Sm', 'Ho'), ('Pr', 'Sm', 'Er'), ('Pr', 'Sm', 'Tm'), ('Pr', 'Sm', 'Yb'), ('Pr', 'Sm', 'Lu'), ('Pr', 'Eu', 'Gd'), ('Pr', 'Eu', 'Tb'), (' Pr', 'Eu', 'Dy'), ('Pr', 'Eu', 'Ho'), ('Pr', 'Eu', 'Er'), ('Pr', 'Eu', 'Tm'), ('Pr', 'Eu', 'Yb'), ('Pr', 'Eu', 'Lu'), (' Pr', 'Gd', 'Tb'), ('Pr', 'Gd', 'Dy'), ('Pr', 'Gd', 'Ho'), ('Pr', 'Gd', 'Er'), ('Pr', 'Gd', 'Tm'), ('Pr', 'Gd', 'Yb'), ('Pr', 'Gd', 'Lu'), ('Pr', 'Tb', 'Dy'), ('Pr', 'Tb', 'Ho'), ('Pr', 'Tb', 'Er'), ('Pr', 'Tb', 'Tm'), ('Pr', 'Tb', 'Yb'), ('Pr', 'Tb', 'Lu'), ('Pr', 'Dy', 'Ho'), ('Pr', 'Dy', 'Er'), ('Pr', 'Dy', 'Tm'), ('Pr', 'Dy', 'Yb'), ('Pr', 'Dy', 'Lu'), ('Pr', 'Ho', 'Er'), ('Pr', 'Ho', 'Tm'), ('Pr', 'Ho', 'Yb'), ('Pr', 'Ho', 'Lu'), ('Pr', 'Er', 'Tm'), ('Pr', 'Er', 'Yb'), ('Pr', 'Er', 'Lu'), ('Pr', 'Tm', 'Yb'), ('Pr', 'Tm', 'Lu'), ('Pr', 'Yb', 'Lu'), ('Nd', 'Sm', 'Eu'), ('Nd', 'Sm', 'Gd'), ('Nd', 'Sm', 'Tb'), ('Nd', 'Sm', 'Dy'), ('Nd', 'Sm', 'Ho'), ('Nd', 'Sm', 'Er'), ('Nd', 'Sm', 'Tm'), ('Nd', ' Sm', 'Yb'), ('Nd', 'Sm', 'Lu'), ('Nd', 'Eu', 'Gd'), ('Nd', 'Eu', 'Tb'), ('Nd', 'Eu', 'Dy'), ('Nd', 'Eu', 'Ho'), (' Nd', 'Eu', 'Er'), ('Nd', 'Eu', 'Tm'), ('Nd', 'Eu', 'Yb'), ('Nd', 'Eu', 'Lu'), ('Nd', 'Gd', 'Tb'), ('Nd', 'Gd', 'D y'), ('Nd', 'Gd', 'Ho'), ('Nd', 'Gd', 'Er'), ('Nd', 'Gd', 'Tm'), ('Nd', 'Gd', 'Yb'), ('Nd', 'Gd', 'Lu'), ('Nd', ' Tb', 'Dy'), ('Nd', 'Tb', 'Ho'), ('Nd', 'Tb', 'Er'), ('Nd', 'Tb', 'Tm'), ('Nd', 'Tb', 'Yb'), ('Nd', 'Tb', 'Lu'), (' Nd', 'Dy', 'Ho'), ('Nd', 'Dy', 'Er'), ('Nd', 'Dy', 'Tm'), ('Nd', 'Dy', 'Yb'), ('Nd', 'Dy', 'Lu'), ('Nd', 'Ho', ' Er'), ('Nd', 'Ho', 'Tm'), ('Nd', 'Ho', 'Yb'), ('Nd', 'Ho', 'Lu'), ('Nd', 'Er', 'Tm'), ('Nd', 'Er', 'Yb'), ('Nd', 'Er', 'Lu'), ('Nd', 'Tm', 'Yb'), ('Nd', 'Tm', 'Lu'), ('Nd', 'Yb', 'Lu'), ('Sm', 'Eu', 'Gd'), ('Sm', 'Eu', 'Tb'), ('Sm', 'Eu', 'Dy'), ('Sm', 'Eu', 'Ho'), ('Sm', 'Eu', 'Er'), ('Sm', 'Eu', 'Tm'), ('Sm', 'Eu', 'Yb'), ('Sm', 'Eu', ' Lu'), ('Sm', 'Gd', 'Tb'), ('Sm', 'Gd', 'Dy'), ('Sm', 'Gd', 'Ho'), ('Sm', 'Gd', 'Er'), ('Sm', 'Gd', 'Tm'), ('Sm', 'Gd', 'Yb'), ('Sm', 'Gd', 'Lu'), ('Sm', 'Tb', 'Dy'), ('Sm', 'Tb', 'Ho'), ('Sm', 'Tb', 'Er'), ('Sm', 'Tb', 'Tm'), ('Sm', 'Tb', 'Yb'), ('Sm', 'Tb', 'Lu'), ('Sm', 'Dy', 'Ho'), ('Sm', 'Dy', 'Er'), ('Sm', 'Dy', 'Tm'), ('Sm', 'D y', 'Yb'), ('Sm', 'Dy', 'Lu'), ('Sm', 'Ho', 'Er'), ('Sm', 'Ho', 'Tm'), ('Sm', 'Ho', 'Yb'), ('Sm', 'Ho', 'Lu'), (' Sm', 'Er', 'Tm'), ('Sm', 'Er', 'Yb'), ('Sm', 'Er', 'Lu'), ('Sm', 'Tm', 'Yb'), ('Sm', 'Tm', 'Lu'), ('Sm', 'Yb', ' Lu'), ('Eu', 'Gd', 'Tb'), ('Eu', 'Gd', 'Dy'), ('Eu', 'Gd', 'Ho'), ('Eu', 'Gd', 'Er'), ('Eu', 'Gd', 'Tm'), ('Eu', ' Gd', 'Yb'), ('Eu', 'Gd', 'Lu'), ('Eu', 'Tb', 'Dy'), ('Eu', 'Tb', 'Ho'), ('Eu', 'Tb', 'Er'), ('Eu', 'Tb', 'Tm'), ('Eu', 'Tb', 'Yb'), ('Eu', 'Tb', 'Lu'), ('Eu', 'Dy', 'Ho'), ('Eu', 'Dy', 'Er'), ('Eu', 'Dy', 'Tm'), ('Eu', 'Dy', 'Yb'), ('Eu', 'Dy', 'Lu'), ('Eu', 'Ho', 'Er'), ('Eu', 'Ho', 'Tm'), ('Eu', 'Ho', 'Yb'), ('Eu', 'Ho', 'Lu'), ('Eu', 'Er', 'T m'), ('Eu', 'Er', 'Yb'), ('Eu', 'Er', 'Lu'), ('Eu', 'Tm', 'Yb'), ('Eu', 'Tm', 'Lu'), ('Eu', 'Yb', 'Lu'), ('Gd', 'Tb', 'Dy'), ('Gd', 'Tb', 'Ho'), ('Gd', 'Tb', 'Er'), ('Gd', 'Tb', 'Tm'), ('Gd', 'Tb', 'Yb'), ('Gd', 'Tb', 'Lu'), ('Gd', 'Dy', 'Ho'), ('Gd', 'Dy', 'Er'), ('Gd', 'Dy', 'Tm'), ('Gd', 'Dy', 'Yb'), ('Gd', 'Dy', 'Lu'), ('Gd', 'Ho', 'Er'), ('Gd', 'Ho', 'Tm'), ('Gd', 'Ho', 'Yb'), ('Gd', 'Ho', 'Lu'), ('Gd', 'Er', 'Tm'), ('Gd', 'Er', 'Yb'), ('Gd', 'Er', 'Lu'), ('Gd', 'Tm', 'Yb'), ('Gd', 'Tm', 'Lu'), ('Gd', 'Yb', 'Lu'), ('Tb', 'Dy', 'Ho'), ('Tb', 'Dy', 'Er'), ('Tb', ' Dy', 'Tm'), ('Tb', 'Dy', 'Yb'), ('Tb', 'Dy', 'Lu'), ('Tb', 'Ho', 'Er'), ('Tb', 'Ho', 'Tm'), ('Tb', 'Ho', 'Yb'), ('Tb', 'Ho', 'Lu'), ('Tb', 'Er', 'Tm'), ('Tb', 'Er', 'Yb'), ('Tb', 'Er', 'Lu'), ('Tb', 'Tm', 'Yb'), ('Tb', 'Tm', 'Lu'), ('Tb', 'Yb', 'Lu'), ('Dy', 'Ho', 'Er'), ('Dy', 'Ho', 'Tm'), ('Dy', 'Ho', 'Yb'), ('Dy', 'Ho', 'Lu'), ('Dy', 'Er', 'Tm'), ('Dy', 'Er', 'Yb'), ('Dy', 'Er', 'Lu'), ('Dy', 'Tm', 'Yb'), ('Dy', 'Tm', 'Lu'), ('Dy', 'Yb', 'Lu'), ('Ho', 'Er', 'Tm'), ('Ho', 'Er', 'Yb'), ('Ho', 'Er', 'Lu'), ('Ho', 'Tm', 'Yb'), ('Ho', 'Tm', 'Lu'), ('Ho', 'Yb', 'Lu'), ('Er', 'Tm', 'Yb'), ('Er', 'Tm', 'Lu'), ('Er', 'Yb', 'Lu'), ('Tm', 'Yb', 'Lu')

3. Example Verification methodology 3: this methodology expands on Verification methodology 2 by the use of naturally occurring microbial cation exchangers, including bacteria and fungi.

i. As above but right before step vii (unsealing samples in laboratory), add the following steps:
ii. Lyse the microbes. For example, autoclave each sample-containing beaker for steam sterilization at 250° F. at 15 psi for 15 minutes. This may lyse any microbes and cause an active release of bio-adsorbed metals.
iii. Let sample-containing beakers cool to room temperature before proceeding.
iv. The filter in step (ix) may now act to additionally remove any larger aggregates of microbial cell suspensions that did not lyse in the autoclaving process.
v. The added EDTA in step (x) in Verification Methodology 2 may act to additionally chelate any REEs that are complexed to the cell wall or organic molecules of the microbial genetic material (as a result of cell lysis).
vi. In conjunction, verification methodology 3 provides a protocol to achieve full recovery of REEs that were retained in the top 10 cm of soil due to the following biogeochemical processes:
1. Mineral surface interface complexation.
2. The cation exchange capacity inherent to soils due to organic matter.
3. Microbially mediated surface biosorption and/or active biological absorption pathways including but not limited to REE-aqueous complexation with internal genetic material of individual microbial cells found in natural soils and sediments.

B. Example Systems and Methods to Enhance the Agronomic Performance and Ecosystem Co-Benefits:

In these non-limiting embodiments, product formulations are detailed that improve the soil quality for improved agronomic applications as well as embodiments that specify improvements on crop health and an ability for plants to protect themselves from pathogens.

Addition of macronutrients that enhance the agronomic benefits of the applied mineral. Example: addition of elemental 1-5% by weight formulation K or Ca or inexpensive REE such as La to improve use cases of pulverized $Mg_2SiO_4$ by improving the nutrient balance of the soil to match the needs of actively growing plants. Application rates for K and Ca may range from 50-100 ppm and lanthanide addition rates may range from 1-50 ppm.

The 1-5% by volume addition of slow-release acidifiers in the form of elements that maintain the acidity of the soil despite the tendency of the applied mineral to reduce soil acidity in the weathering process. Example: addition of minerals with Al (such as gibbsite, $Al(OH)_3$) or S (such as gypsum, $CaSO_4$)-$2H_2O$), in a rate of 1-10% by weight of total formulation, which contribute to maintaining soil acidity, and thus maintain high rates of weathering, which counteracts the tendency of forsterite weathering to increase alkalinity, which slows rates of weathering.

The incorporation of additional micronutrients such as zinc (1-5% by weight compared to mineral amendment) to reduce ecosystem losses of phosphorus and downstream ecosystem impacts of phosphate-based fertilizers, such as eutrophication. Phosphates are immobilized via precipitation reactions with the additional zinc metal, so zinc addition slows the transport and reduces mobility of phosphate in the subsoil. As a consequence, phosphate-based fertilizer applications can be performed more safely and with higher confidence that downstream waterways will not form algal blooms and lead to anoxic, uninhabitable waterways for aquatic life. The addition of 1-32 tons/hectare of mineral in conjunction with 1-5% by weight zinc in fields with heavy phosphate application reduces the likelihood of significant phosphate leaching. This also increases nutrient use efficiency, which reduces fertilizer cost to farmers and reduces negative environmental impacts to society. Specifically, phosphate-zinc precipitates become slow-releasing over time due to their immobilization in the soil as a solid phase. This provides longer timeframes for plants to access the phosphate application, reducing the frequency of fertilization.

The method of mixing of different mineral adjuvants to the primary mineral used for carbon removal can be varied, with impacts on performance. In some embodiments, the admixture (e.g., of gypsum and forsterite) could be completely emulsified. In some embodiments, a nutrient, such as urea, could represent a core that is subsequently coated with a shell of silicate mineral used for carbon removal. In some embodiments the silicate mineral could be the core, and the nutrient, such as urea, could be the coating. In each of these cases, the embodiment can be optimized so as to reduce environmental losses of the nutrient, and increase availability to the plant, while providing the acidity necessary for the silicate mineral weathering. In some embodiments, this may represent a "slow release" nutrient that does not mineralize too quickly and is synchronized more favorably with plant demand.

Figure 2:
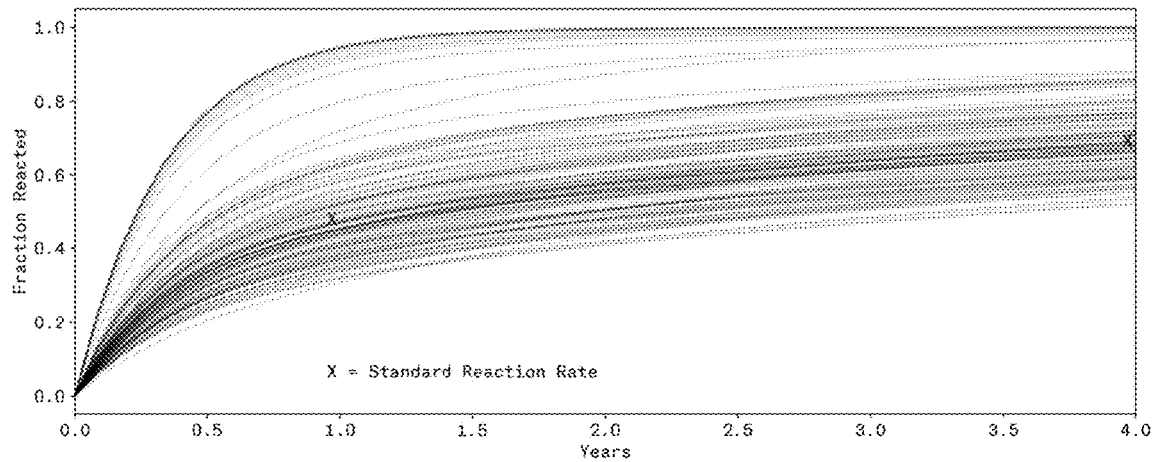
FIG. 2 is a graph depicting the effect of comminution on dissolution kinetics for a silicate.
Figure 3A:
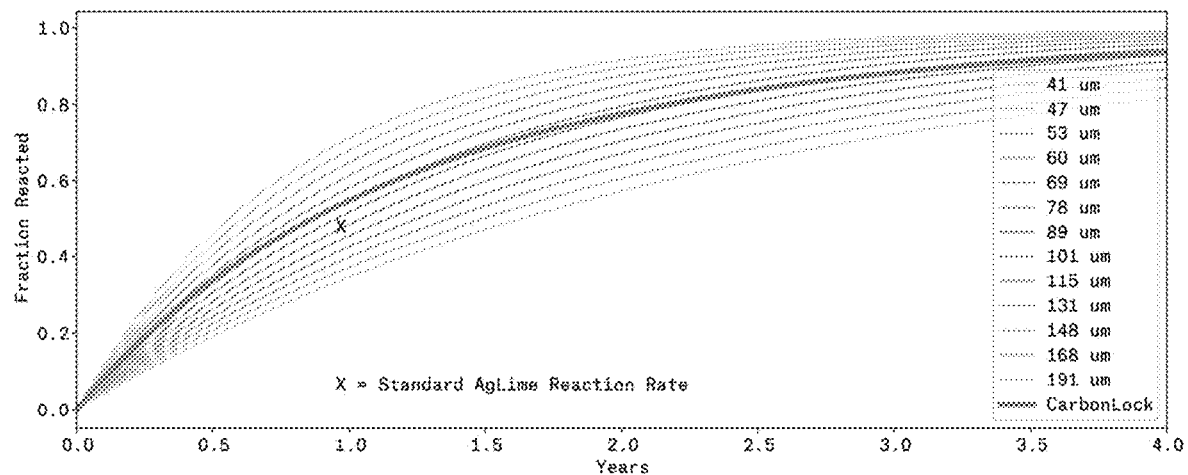
FIGS. 3A to 3D are graphs depicting the kinetics for a particle size distribution of a pulverized silicate with median particle size of 80-100 um which closely approximates the alkalinity release dynamics for aglime.
Figure 3B:
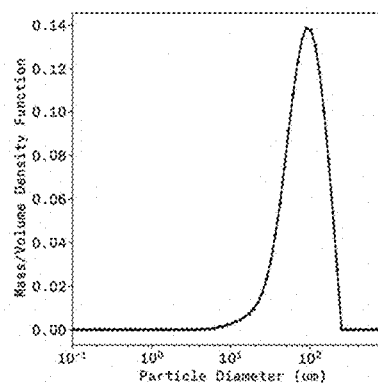
Figure 3C:
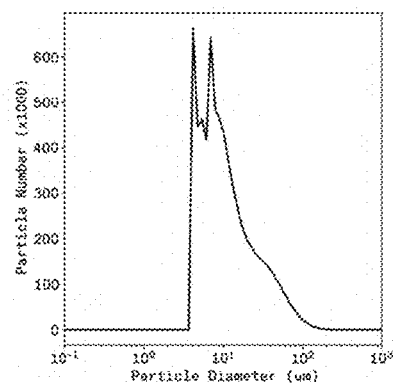
Figure 3D:
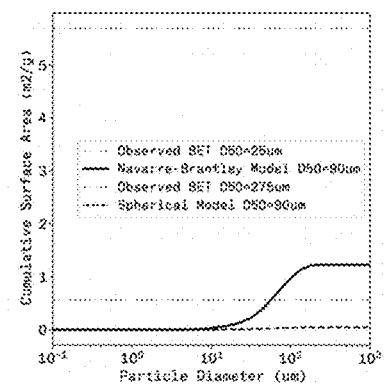

Comminution, or pulverization, may help reproduce the expected kinetics of alkalizers such as pulverized limestone or dolomite, known as aglime. Aglime has well-characterized kinetics originating in the particle size distribution of the product, which are in some jurisdictions legally regulated to meet certain requirements. A representative cross section of dissolution kinetics based on actual aglime mesh size observations is depicted in FIG. 2.

It naturally follows that agronomic performance expectations for silicate minerals used for ERW should follow similar reaction kinetics, particularly in the first year after application, while also meeting the goals for CDR. Thus, an ideal particle size distribution may be tuned to meet this goal. The following shows the kinetics for a particle size distribution of a pulverized silicate with median particle size of 80-100 um, such as 90 um, which closely approximates the alkalinity release dynamics for aglime.

The small particle sizes produced by pulverization as above are valuable for performance as an aglime substitute and CDR mechanism, but introduce their own set of potential challenges. One potential challenge is that small particle sizes may fall within regulated categories such as PM10 or PM2.5; another potential challenge is the product may not be easily transferred from one vessel to another (so-called "flowability") because it has a tendency to settle into a compact mass; the product may also not be applied uniformly by extant farm equipment; potentially low uniformity application impacts the agronomic performance as well as the sampling density needed for carbon removal verification. In one potential formulation, the product is pelletized after pulverization, using a common binder such as lignosulfate in a 3-5% ratio by weight of the total formulation. The amount of binder may be optimized to improve performance characteristics during transport and application, but minimize the water and energy needed to dissolve the pellet once it is in the field. Pelletizing the product, into a size range of, for example, 0.5 mm to 3 mm increases the flowability; reduces the prevalence of dust, including the risk of asbestos exposure; enables the use of extant crop input application equipment; and improves the evenness of field distribution, which has the agronomic and carbon verification benefits identified. Pelletizing in this size range also ensures that an adequate number of pellets fall onto any land area which may subsequently be sampled for analysis.

A desiccated but living biological compound, such as a mycorrhizal inoculum, may be used to coat the agglomerated and dried pellets, so as to enhance the dissolution of the pellet itself after application. This may be distinct from a fungal adjuvant to the pellet to increase dissolution of the silicate minerals themselves.

To accommodate a range of soil types from acidic to neutral pH, the product may be differentiated into different particle size distributions so as to achieve a consistent rate of weathering across different soil types. For example a consistent rate of weathering may be that the entire applied amount of mineral product weathers in 9 months, allowing a subsequent application every year. To achieve this, an acidic soil may have pellets that contain particles with a modal size on the order of 100 um, while a neutral soil may have pellets that contain particles with a modal size on the order of 10 um. The negative consequence of applying a fine particle in an acidic soil may be that it dissolves too quickly, swinging the pH of the soil too quickly, and altering the nutrient availability severely in the growing plant. The negative consequence of applying a coarse particle in a neutral soil may be that the particle weathers too slowly or is functionally inert, which does not remove carbon as intended, and may subject the farmer or the vendor to risk of clawbacks for payments received for carbon removal.

Figure 4:
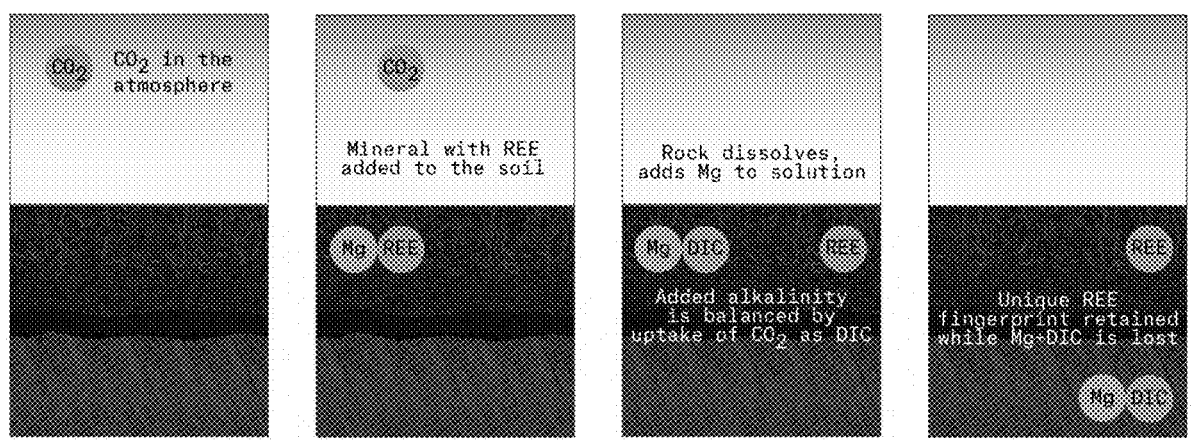
FIG. 4 is a drawing illustrating the general scheme for a verified enhanced rock weathering cycle.

C. Example Systems and Methods to Control or Enhance the Performance as a Securitized Carbon Removal Method:

In these non-limiting embodiments, product formulations are described that improve the marketability of pulverized and optionally pelletized mineral amendments as a verifiable carbon removal method, irrespective of their impact on agronomic performance. Such changes in marketability increase the value of the carbon product, for example for detecting and preventing fraud, or increase the dissolution rate (mass per area per year) to accelerate the timing of reapplication, which raises the value in a discounted cash flow analysis. The general scheme is depicted in FIG. 4.

The addition of low cost and inert trace elements, for example 1-5 ppm neodymium or lanthanum, to a mineral amendment, beyond the natural abundances present in the ore body, improves performance in Verification methods 2 and 3. Specifically, the additional elements reduce measurement uncertainty owing to low natural abundance calculations as well as uncertainty owing to variability from the source mineral. Reduction of these uncertainties improves the detectability of true positives and true negatives. This principle could be applied to many potential soil amendments and fertilizers to verify provenance as pertains to legal contracts.

The addition of binders to create aggregations of the ground mineral that could reduce drift, which improves distribution uniformity; reduces potential respiratory health impacts; and/or improves applicability of the applied mineral using commercially available equipment. For example, a biofilm mediating organic compound, such as alginate or chitosan, could be mixed with a pulverized mineral with a particle size of approximately 100 microns to achieve an aggregated pellet size of 1 millimeter. This would maintain the advantages of fine particle size, particularly the high specific surface area ($m^2/g$) that mediates dissolution rate, while offsetting potential limitations outlined above. An example methodology for aggregating ground minerals could include these steps:

Dissolve 10 grams of alginate powder into solution to create a 0.5 M-1.0 M alginic acid solution.

Heat solution to 80-100° F. to dissolve alginate powder fully if necessary.

Spray aerosol sized particles of dissolved alginate powder onto the ground rock material in order to create a biofilm-coated rock material. Apply a consistent spray of 100 mL for each 100 gram of rock (1:1 v/w).

The resulting aggregates may have increased bulk density as well as higher aggregating properties due to van der Waals force attraction between the individual rock particles.

Dissolution rates can be modified by non-living organic molecules applied concurrently with the mineral amendment. For example, protonated microbes such as acid-treated *Arthrobacter nicotianae* can constitute an initial release of protons to attack the ground rock materials' crystal structure. This method of acidification for optimal accelerated weathering of rock material may occur even during winter/cold climate. Because biologically mediated processes can have sharp thresholds, e.g., under freezing conditions, such a chemically controlled process would exhibit greater ability to expedite rock breakdown over a range of environmental conditions. To implement this methodology, we outline the following steps:

1) De-frost an aliquot of *A. nicotianae* in 5 mL of Luria broth for about 24 hours at exactly 30° C.
2) Sub-culture into a larger volume of Luria broth at a 1:50 dilution and allow growth for another 24 hours at 30° C.
3) During growth steps #1 and 2, cultures may be shaken, for example at 200-220 RPM, for aeration.
4) After culture has been grown for 48 hours in total, centrifuge the cell suspension.
5) Collect cell pellet and take a small amount and set it aside. Weigh wet weight, dry 60° C. overnight, and weigh dry amount to obtain wet: dry conversion.
6) Develop an $OD_{600}$ to wet weight to dry weight conversion by taking 5 varying amounts of wet aliquots of wet biomass and measuring optical density given its known wet mass. Wet aliquots may have a mass of about 1, 4, 8, 12, 16 wet grams and be suspended in 100 mL of DI water.
7) Wash cells in 0.1 M NaCl solution.
   a. Centrifuge cells+growth media at 4000×g.
   b. Carefully pour out LB broth.
   c. Add 0.1 M NaCl solution.
   d. Centrifuge cells+NaCl solution at 4000×g.
   e. Carefully pour out NaCl solution.
8) Protonate the cells while wet.
   a. Re-suspend the wet biomass in an acidic (e.g., pH 3.0) solution using a dilute hydrochloric acid solution (0.001-0.01 M).
   b. Centrifuge cells+HCl solution at 4000×g.
   c. Carefully pour out solution.
   d. Repeat steps (a)-(c) a total of three times.
   e. Dry cells in an oven at 80-100° C. for 48 hours.
   f. Grind cells using a mortar/pestle to achieve a powder form.
9) Mix 5% w/w of dry cell powder with the ground rock material.
10) When this particular rock material+cell powder mixture is applied to agricultural soils, the irrigation or rainfall will re-apply moisture and allow the pre-protonated, re-wet biomass to release their protons. This will ultimately induce a local acidity effect on the rock particle (molecular) level to accelerate rock crystal lattice breakdown. The cells act as biodegradable transporters that are also benign to the natural soil environment.

What is claimed is:

1. A method for verifying enhanced rock weathering using a mineral amendment comprising:

measuring one or more immobile trace elements in a mineral amendment, the immobile trace elements comprising one or more rare earth elements, rare metals, or transition metals; and subsequently measuring the immobile trace elements in a soil sample after application of the mineral amendment to verify application of the mineral amendment.

2. The method of claim 1, further comprising the step of determining the amount of the mineral amendment added to the soil sample.

3. The method of claim 1, further comprising the step of determining the amount of measured divalent cations in the soil sample.

4. The method of claim 3, further comprising the step of determining a fractional carbon dioxide removal by comparing a calculated amount of applied divalent cations to the measured divalent cations in the soil sample.

5. The method of claim 1, wherein the immobile trace elements and magnesium are measured using inductively coupled plasma spectroscopy or x-ray fluorescence spectroscopy.

6. The method of claim 1, further comprising the step of measuring the immobile trace elements in the soil sample prior to addition of the mineral amendment.

7. The method of claim 1, further comprising the step of enriching the abundance of the immobile trace elements in the mineral amendment.

8. The method of claim 1, wherein:

the rare earth elements comprise scandium (Sc), yttrium (Y), lanthanum (La), cerium (Ce), praseodymium (Pr), neodymium (Nd), samarium (Sm), europium (Eu), gadolinium (Gd), terbium (Tb), dysprosium (Dy), holmium (Ho), erbium (Er), thulium (Tm), ytterbium (Yb), and lutetium (Lu);

the rare metals comprise beryllium (Be), cesium (Cs), gallium (Ga), germanium (Ge), hafnium (Hf), niobium (Nb), rubidium (Rb), tantalum (Ta), titanium (Ti), vanadium (V), and zirconium (Zr); and the transition metals comprise nickel (Ni), chromium (Cr), and zinc (Zn).

9. The method of claim 1, wherein three immobile trace elements are measured.

10. The method of claim 9, wherein the three immobile trace elements are selected from the list comprising: ('Y', 'La', 'Ce'), ('Y', 'La', 'Pr'), ('Y', 'La', 'Nd'), ('Y', 'La', 'Sm'), ('Y', 'La', 'Eu'), ('Y', 'La', 'Gd'), ('Y', 'La', 'Tb'), ('Y', 'La', 'Dy'), ('Y', 'La', 'Ho'), ('Y', 'La', 'Er'), ('Y', 'La', 'Tm'), ('Y', 'La', 'Yb'), ('Y', 'La', 'Lu'), ('Y', 'Ce', 'Pr'), ('Y', 'Ce', 'Nd'), ('Y', 'Ce', 'Sm'), ('Y', 'Ce', 'Eu'), ('Y', 'Ce', 'Gd'), ('Y', 'Ce', 'Tb'), ('Y', 'Ce', 'Dy'), ('Y', 'Ce', 'Ho'), ('Y', 'Ce', 'Er'), ('Y', 'Ce', 'Tm'), ('Y', 'Ce', 'Yb'), ('Y', 'Ce', 'Lu'), ('Y', 'Pr', 'Nd'), ('Y', 'Pr', 'Sm'), ('Y', 'Pr', 'Eu'), ('Y', 'Pr', 'Gd'), ('Y', 'Pr', 'Tb'), ('Y', 'Pr', 'Dy'), ('Y', 'Pr', 'Ho'), ('Y', 'Pr', 'Er'), ('Y', 'Pr', 'Tm'), ('Y', 'Pr', 'Yb'), ('Y', 'Pr', 'Lu'), ('Y', 'Nd', 'Sm'), ('Y', 'Nd', 'Eu'), ('Y', 'Nd', 'Gd'), ('Y', 'Nd', 'Tb'), ('Y', 'Nd', 'Dy'), ('Y', 'Nd', 'Ho'), ('Y', 'Nd', 'Er'), ('Y', 'Nd', 'Tm'), ('Y', 'Nd', 'Yb'), ('Y', 'Nd', 'Lu'), ('Y', 'Sm', 'Eu'), ('Y', 'Sm', 'Gd'), ('Y', 'Sm', 'Tb'), ('Y', 'Sm', 'Dy'), ('Y', 'Sm', 'Ho'), ('Y', 'Sm', 'Er'), ('Y', 'Sm', 'Tm'), ('Y', 'Sm', 'Yb'), ('Y', 'Sm', 'Lu'), ('Y', 'Eu', 'Gd'), ('Y', 'Eu', 'Tb'), ('Y', 'Eu', 'Dy'), ('Y', 'Eu', 'Ho'), ('Y', 'Eu', 'Er'), ('Y', 'Eu', 'Tm'), ('Y', 'Eu', 'Yb'), ('Y', 'Eu', 'Lu'), ('Y', 'Gd', 'Tb'), ('Y', 'Gd', 'Dy'), ('Y', 'Gd', 'Ho'), ('Y', 'Gd', 'Er'), ('Y', 'Gd', 'Tm'), ('Y', 'Gd', 'Yb'), ('Y', 'Gd', 'Lu'), ('Y', 'Tb', 'Dy'), ('Y', 'Tb', 'Ho'), ('Y', 'Tb', 'Er'), ('Y', 'Tb', 'Tm'), ('Y', 'Tb', 'Yb'), ('Y', 'Tb', 'Lu'), ('Y', 'Dy', 'Ho'), ('Y', 'Dy', 'Er'), ('Y', 'Dy', 'Tm'), ('Y', 'Dy', 'Yb'), ('Y', 'Dy', 'Lu'), ('Y', 'Ho', 'Er'), ('Y', 'Ho', 'Tm'), ('Y', 'Ho', 'Yb'), ('Y', 'Ho', 'Lu'), ('Y', 'Er', 'Tm'), ('Y', 'Er', 'Yb'), ('Y', 'Er', 'Lu'), ('Y', 'Tm', 'Yb'), ('Y', 'Tm', 'Lu'), ('Y', 'Yb', 'Lu'), ('La', 'Ce', 'Pr'), ('La', 'Ce', 'Nd'), ('La', 'Ce', 'Sm'), ('La', 'Ce', 'Eu'), ('La', 'Ce', 'Gd'), ('La', 'Ce', 'Tb'), ('La', 'Ce', 'Dy'), ('La', 'Ce', 'Ho'), ('La', 'Ce', 'Er'), ('La', 'Ce', 'Tm'), ('La', 'Ce', 'Yb'), ('La', 'Ce', 'Lu'), ('La', 'Pr', 'Nd'), ('La', 'Pr', 'Sm'), ('La', 'Pr', 'Eu'), ('La', 'Pr', 'Gd'), ('La', 'Pr', 'Tb'), ('La', 'Pr', 'Dy'), ('La', 'Pr', 'Ho'), ('La', 'Pr', 'Er'), ('La', 'Pr', 'Tm'), ('La', 'Pr', 'Yb'), ('La', 'Pr', 'Lu'), ('La', 'Nd', 'Sm'), ('La', 'Nd', 'Eu'), ('La', 'Nd', 'Gd'), ('La', 'Nd', 'Tb'), ('La', 'Nd', 'Dy'), ('La', 'Nd', 'Ho'), ('La', 'Nd', 'Er'), ('La', 'Nd', 'Tm'), ('La', 'Nd', 'Yb'), ('La', 'Nd', 'Lu'), ('La', 'Sm', 'Eu'), ('La', 'Sm', 'Gd'), ('La', 'Sm', 'Tb'), ('La', 'Sm', 'Dy'), ('La', 'Sm', 'Ho'), ('La', 'Sm', 'Er'), ('La', 'Sm', 'Tm'), ('La', 'Sm', 'Yb'), ('La', 'Sm', 'Lu'), ('La', 'Eu', 'Gd'), ('La', 'Eu', 'Tb'), ('La', 'Eu', 'Dy'), ('La', 'Eu', 'Ho'), ('La', 'Eu', 'Er'), ('La', 'Eu', 'Tm'), ('La', 'Eu', 'Yb'), ('La', 'Eu', 'Lu'), ('La', 'Gd', 'Tb'), ('La', 'Gd', 'Dy'), ('La', 'Gd', 'Ho'), ('La', 'Gd', 'Er'), ('La', 'Gd', 'Tm'), ('La', 'Gd', 'Yb'), ('La', 'Gd', 'Lu'), ('La', 'Tb', 'Dy'), ('La', 'Tb', 'Ho'), ('La', 'Tb', 'Er'), ('La', 'Tb', 'Tm'), ('La', 'Tb', 'Yb'), ('La', 'Tb', 'Lu'), ('La', 'Dy', 'Ho'), ('La', 'Dy', 'Er'), ('La', 'Dy', 'Tm'), ('La', 'Dy', 'Yb'), ('La', 'Dy', 'Lu'), ('La', 'Ho', 'Er'), ('La', 'Ho', 'Tm'), ('La', 'Ho', 'Yb'), ('La', 'Ho', 'Lu'), ('La', 'Er', 'Tm'), ('La', 'Er', 'Yb'), ('La', 'Er', 'Lu'), ('La', 'Tm', 'Yb'), ('La', 'Tm', 'Lu'), ('La', 'Yb', 'Lu'), ('Ce', 'Pr', 'Nd'), ('Ce', 'Pr', 'Sm'), ('Ce', 'Pr', 'Eu'), ('Ce', 'Pr', 'Gd'), ('Ce', 'Pr', 'Tb'), ('Ce', 'Pr', 'Dy'), ('Ce', 'Pr', 'Ho'), ('Ce', 'Pr', 'Er'), ('Ce', 'Pr', 'Tm'), ('Ce', 'Pr', 'Yb'), ('Ce', 'Pr', 'Lu'), ('Ce', 'Nd', 'Sm'), ('Ce', 'Nd', 'Eu'), ('Ce', 'Nd', 'Gd'), ('Ce', 'Nd', 'Tb'), ('Ce', 'Nd', 'Dy'), ('Ce', 'Nd', 'Ho'), ('Ce', 'Nd', 'Er'), ('Ce', 'Nd', 'Tm'), ('Ce', 'Nd', 'Yb'), ('Ce', 'Nd', 'Lu'), ('Ce', 'Sm', 'Eu'), ('Ce', 'Sm', 'Gd'), ('Ce', 'Sm', 'Tb'), ('Ce', 'Sm', 'Dy'), ('Ce', 'Sm', 'Ho'), ('Ce', 'Sm', 'Er'), ('Ce', 'Sm', 'Yb'), ('Ce', 'Sm', 'Tm'), ('Ce', 'Sm', 'Lu'), ('Ce', 'Eu', 'Gd'), ('Ce', 'Eu', 'Tb'), ('Ce', 'Eu', 'Dy'), ('Ce', 'Eu', 'Ho'), ('Ce', 'Eu', 'Er'), ('Ce', 'Eu', 'Tm'), ('Ce', 'Eu', 'Yb'), ('Ce', 'Eu', 'Lu'), ('Ce', 'Gd', 'Tb'), ('Ce', 'Gd', 'Dy'), ('Ce', 'Gd', 'Ho'), ('Ce', 'Gd', 'Er'), ('Ce', 'Gd', 'Tm'), ('Ce', 'Gd', 'Yb'), ('Ce', 'Gd', 'Lu'), ('Ce', 'Tb', 'Dy'), ('Ce', 'Tb', 'Ho'), ('Ce', 'Tb', 'Er'), ('Ce', 'Tb', 'Tm'), ('Ce', 'Tb', 'Yb'), ('Ce', 'Tb', 'Lu'), ('Ce', 'Dy', 'Ho'), ('Ce', 'Dy', 'Er'), ('Ce', 'Dy', 'Tm'), ('Ce', 'Dy', 'Yb'), ('Ce', 'Dy', 'Lu'), ('Ce', 'Ho', 'Er'), ('Ce', 'Ho', 'Tm'), ('Ce', 'Ho', 'Yb'), ('Ce', 'Ho', 'Lu'), ('Ce', 'Er', 'Tm'), ('Ce', 'Er', 'Yb'), ('Ce', 'Er', 'Lu'), ('Ce', 'Tm', 'Yb'), ('Ce', 'Tm', 'Lu'), ('Ce', 'Yb', 'Lu'), ('Pr', 'Nd', 'Sm'), ('Pr', 'Nd', 'Eu'), ('Pr', 'Nd', 'Gd'), ('Pr', 'Nd', 'Tb'), ('Pr', 'Nd', 'Dy'), ('Pr', 'Nd', 'Ho'), ('Pr', 'Nd', 'Er'), ('Pr', 'Nd', 'Tm'), ('Pr', 'Nd', 'Yb'), ('Pr', 'Nd', 'Lu'), ('Pr', 'Sm', 'Eu'), ('Pr', 'Sm', 'Gd'), ('Pr', 'Sm', 'Tb'), ('Pr', 'Sm', 'Dy'), ('Pr', 'Sm', 'Ho'), ('Pr', 'Sm', 'Er'), ('Pr', 'Sm', 'Tm'), ('Pr', 'Sm', 'Yb'), ('Pr', 'Sm', 'Lu'), ('Pr', 'Eu', 'Gd'), ('Pr', 'Eu', 'Tb'), ('Pr', 'Eu', 'Dy'), ('Pr', 'Eu', 'Ho'), ('Pr', 'Eu', 'Er'), ('Pr', 'Eu', 'Tm'), ('Pr', 'Eu', 'Yb'), ('Pr', 'Eu', 'Lu'), ('Pr', 'Gd', 'Tb'), ('Pr', 'Gd', 'Dy'), ('Pr', 'Gd', 'Ho'), ('Pr', 'Gd', 'Er'), ('Pr', 'Gd', 'Tm'), ('Pr', 'Gd', 'Yb'), ('Pr', 'Gd', 'Lu'), ('Pr', 'Tb', 'Dy'), ('Pr', 'Tb', 'Ho'), ('Pr', 'Tb', 'Er'), ('Pr', 'Tb', 'Tm'), ('Pr', 'Tb', 'Yb'), ('Pr', 'Tb', 'Lu'), ('Pr', 'Dy', 'Ho'), ('Pr', 'Dy', 'Er'), ('Pr', 'Dy', 'Tm'), ('Pr', 'Dy', 'Yb'), ('Pr', 'Dy', 'Lu'), ('Pr', 'Ho', 'Er'), ('Pr', 'Ho', 'Tm'), ('Pr', 'Ho', 'Yb'), ('Pr', 'Ho', 'Lu'), ('Pr', 'Er', 'Tm'), ('Pr', 'Er', 'Yb'), ('Pr', 'Er', 'Lu'), ('Pr', 'Tm', 'Yb'), ('Pr', 'Tm', 'Lu'), ('Pr', 'Yb', 'Lu'), ('Nd', 'Sm', 'Eu'), ('Nd', 'Sm', 'Gd'), ('Nd', 'Sm', 'Tb'), ('Nd', 'Sm', 'Dy'), ('Nd', 'Sm', 'Ho'), ('Nd', 'Sm', 'Er'), ('Nd', 'Sm', 'Tm'), ('Nd', 'Sm', 'Yb'), ('Nd', 'Sm', 'Lu'), ('Nd', 'Eu', 'Gd'), ('Nd', 'Eu', 'Tb'), ('Nd', 'Eu', 'Dy'), ('Nd', 'Eu', 'Ho'), ('Nd', 'Eu', 'Er'), ('Nd', 'Eu', 'Tm'), ('Nd', 'Eu', 'Yb'), ('Nd', 'Eu', 'Lu'), ('Nd', 'Gd', 'Tb'), ('Nd', 'Gd', 'Dy'), ('Nd', 'Gd', 'Ho'), ('Nd', 'Gd', 'Er'), ('Nd', 'Gd', 'Tm'), ('Nd', 'Gd', 'Yb'), ('Nd', 'Gd', 'Lu'), ('Nd', 'Tb', 'Dy'), ('Nd', 'Tb', 'Ho'), ('Nd', 'Tb', 'Er'), ('Nd', 'Tb', 'Tm'), ('Nd', 'Tb', 'Yb'), ('Nd', 'Tb', 'Lu'), ('Nd', 'Dy', 'Ho'), ('Nd', 'Dy', 'Er'), ('Nd', 'Dy', 'Tm'), ('Nd', 'Dy', 'Yb'), ('Nd', 'Dy', 'Lu'), ('Nd', 'Ho', 'Er'), ('Nd', 'Ho', 'Tm'), ('Nd', 'Ho', 'Yb'), ('Nd', 'Ho', 'Lu'), ('Nd', 'Er', 'Tm'), ('Nd', 'Er', 'Yb'), ('Nd', 'Er', 'Lu'), ('Nd', 'Tm', 'Yb'), ('Nd', 'Tm', 'Lu'), ('Nd', 'Yb', 'Lu'), ('Sm', 'Eu', 'Gd'), ('Sm', 'Eu', 'Tb'), ('Sm', 'Eu', 'Dy'), ('Sm', 'Eu', 'Ho'), ('Sm', 'Eu', 'Er'), ('Sm', 'Eu', 'Tm'), ('Sm', 'Eu', 'Yb'), ('Sm', 'Eu', 'Lu'), ('Sm', 'Gd', 'Tb'), ('Sm', 'Gd', 'Dy'), ('Sm', 'Gd', 'Ho'), ('Sm', 'Gd', 'Er'), ('Sm', 'Gd', 'Tm'), ('Sm', 'Gd', 'Yb'), ('Sm', 'Gd', 'Lu'), ('Sm', 'Tb', 'Dy'), ('Sm', 'Tb', 'Ho'), ('Sm', 'Tb', 'Er'), ('Sm', 'Tb', 'Tm'), ('Sm', 'Tb', 'Yb'), ('Sm', 'Tb', 'Lu'), ('Sm', 'Dy', 'Ho'), ('Sm', 'Dy', 'Er'), ('Sm', 'Dy', 'Tm'), ('Sm', 'Dy', 'Yb'), ('Sm', 'Dy', 'Lu'), ('Sm', 'Ho', 'Er'), ('Sm', 'Ho', 'Tm'), ('Sm', 'Ho', 'Yb'), ('Sm', 'Ho', 'Lu'), ('Sm', 'Er', 'Tm'), ('Sm', 'Er', 'Yb'), ('Sm', 'Er', 'Lu'), ('Sm', 'Tm', 'Yb'), ('Sm', 'Tm', 'Lu'), ('Sm', 'Yb', 'Lu'), ('Eu', 'Gd', 'Tb'), ('Eu', 'Gd', 'Dy'), ('Eu', 'Gd', 'Ho'), ('Eu', 'Gd', 'Er'), ('Eu', 'Gd', 'Tm'), ('Eu', 'Gd', 'Yb'), ('Eu', 'Gd', 'Lu'), ('Eu', 'Tb', 'Dy'), ('Eu', 'Tb', 'Ho'), ('Eu', 'Tb', 'Er'), ('Eu', 'Tb', 'Tm'), ('Eu', 'Tb', 'Yb'), ('Eu', 'Tb', 'Lu'), ('Eu', 'Dy', 'Ho'), ('Eu', 'Dy', 'Er'), ('Eu', 'Dy', 'Tm'), ('Eu', 'Dy', 'Yb'), ('Eu', 'Dy', 'Lu'), ('Eu', 'Ho', 'Er'), ('Eu', 'Ho', 'Tm'), ('Eu', 'Ho', 'Yb'), ('Eu', 'Ho', 'Lu'), ('Eu', 'Er', 'Tm'), ('Eu', 'Er', 'Yb'), ('Eu', 'Er', 'Lu'), ('Eu', 'Tm', 'Yb'), ('Eu', 'Tm', 'Lu'), ('Eu', 'Yb', 'Lu'), ('Gd', 'Tb', 'Dy'), ('Gd', 'Tb', 'Ho'), ('Gd', 'Tb', 'Er'), ('Gd', 'Tb', 'Tm'), ('Gd', 'Tb', 'Yb'), ('Gd', 'Tb', 'Lu'), ('Gd', 'Dy', 'Ho'), ('Gd', 'Dy', 'Er'), ('Gd', 'Dy', 'Tm'), ('Gd', 'Dy', 'Yb'), ('Gd', 'Dy', 'Lu'), ('Gd', 'Ho', 'Er'), ('Gd', 'Ho', 'Tm'), ('Gd', 'Ho', 'Yb'), ('Gd', 'Ho', 'Lu'), ('Gd', 'Er', 'Tm'), ('Gd', 'Er', 'Yb'), ('Gd', 'Er', 'Lu'), ('Gd', 'Tm', 'Yb'), ('Gd', 'Tm', 'Lu'), ('Gd', 'Yb', 'Lu'), ('Tb', 'Dy', 'Ho'), ('Tb', 'Dy', 'Er'), ('Tb', 'Dy', 'Tm'), ('Tb', 'Dy', 'Yb'), ('Tb', 'Dy', 'Lu'), ('Tb', 'Ho', 'Er'), ('Tb', 'Ho', 'Tm'), ('Tb', 'Ho', 'Yb'), ('Tb', 'Ho', 'Lu'), ('Tb', 'Er', 'Tm'), ('Tb', 'Er', 'Yb'), ('Tb', 'Er', 'Lu'), ('Tb', 'Tm', 'Yb'), ('Tb', 'Tm', 'Lu'), ('Tb', 'Yb', 'Lu'), ('Dy', 'Ho', 'Er'), ('Dy', 'Ho', 'Tm'), ('Dy', 'Ho', 'Yb'), ('Dy', 'Ho', 'Lu'), ('Dy', 'Er', 'Tm'), ('Dy', 'Er', 'Yb'), ('Dy', 'Er', 'Lu'), ('Dy', 'Tm', 'Yb'), ('Dy', 'Tm', 'Lu'), ('Dy', 'Yb', 'Lu'), ('Ho', 'Er', 'Tm'), ('Ho', 'Er', 'Yb'), ('Ho', 'Er', 'Lu'), ('Ho', 'Tm', 'Yb'), ('Ho', 'Tm', 'Lu'), ('Ho', 'Yb', 'Lu'), ('Er', 'Tm', 'Yb'), ('Er', 'Tm', 'Lu'), ('Er', 'Yb', 'Lu'), and ('Tm', 'Yb', 'Lu').

11. The method of claim 1, wherein the step of measuring the immobile trace elements in a soil sample after application of the mineral amendment further comprises lysing the soil sample and application of ethylenediaminetetraacetic acid.

\* \* \* \* \*